US00PP30685P3

(12) United States Plant Patent
Flore

(10) Patent No.: US PP30,685 P3
(45) Date of Patent: Jul. 9, 2019

(54) ***PHALAENOPSIS* PLANT NAMED 'MI00599'**

(50) Latin Name: *Phalaenopsis hybrida*
Varietal Denomination: MI00599

(71) Applicant: Febe Flore, Lochristi (BE)

(72) Inventor: Febe Flore, Lochristi (BE)

(73) Assignee: Floreac N.V. div. Microflor, Lochristi (BE)

( * ) Notice: Subject to any disclaimer, the term of this patent is extended or adjusted under 35 U.S.C. 154(b) by 0 days.

(21) Appl. No.: 15/732,277

(22) Filed: Oct. 17, 2017

(65) Prior Publication Data

US 2019/0116704 P1 Apr. 18, 2019

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
CPC ..... A01H 6/62; A01H 5/02
See application file for complete search history.

*Primary Examiner* — Keith O. Robinson
(74) *Attorney, Agent, or Firm* — C. A. Whealy

(57) ABSTRACT

A new and distinct cultivar of *Phalaenopsis* plant named 'MI00599', characterized by its upright plant habit; moderately vigorous growth habit; strong flowering stems; freely flowering habit with typically two to three racemes per plant, each inflorescence with numerous flowers; and showy white-colored flowers with red purple-colored venation.

2 Drawing Sheets

Botanical designation: *Phalaenopsis hybrida.*
Cultivar denomination: 'MI00599'.

BACKGROUND OF THE INVENTION

The present invention relates to a new and distinct cultivar of *Phalaenopsis* plant, botanically known as *Phalaenopsis hybrida*, and hereinafter referred to by the name 'MI00599'.

The new *Phalaenopsis* plant is a product of a planned breeding program conducted by the Inventor in Lochristi, Belgium. The objective of the breeding program is to develop new freely flowering *Phalaenopsis* plants with good leaf shape and unique and attractive flower patterns and coloration.

The new *Phalaenopsis* plant originated from a cross-pollination in December, 2008 in Lochristi, Belgium of a proprietary selection of *Phalaenopsis hybrida* identified as code number PH00743, not patented, as the female, or seed, parent with a proprietary selection of *Phalaenopsis hybrida* identified as code number PHM00230, not patented, as the male, or pollen, parent. The new *Phalaenopsis* plant was discovered and selected by the Inventor as a single flowering plant from within the progeny of the stated cross-pollination grown in a controlled greenhouse environment in Lochristi, Belgium in March, 2010.

Asexual reproduction of the new *Phalaenopsis* plant by in vitro propagation (meristem culture) in a controlled environment in Lochristi, Belgium since July, 2012 has shown that the unique features of this new *Phalaenopsis* plant are stable and reproduced true to type in successive generations.

SUMMARY OF THE INVENTION

Plants of the new *Phalaenopsis* have been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'MI00599'. These characteristics in combination distinguish 'MI00599' as a new and distinct *Phalaenopsis* plant:

1. Upright plant habit.
2. Moderately vigorous growth habit.
3. Strong flowering stems.
4. Freely flowering habit with typically two to three racemes per plant, each inflorescence with numerous flowers.
5. Showy white-colored flowers with red purple-colored venation.

Plants of the new *Phalaenopsis* can be compared to plants of the female parent selection. Plants of the new *Phalaenopsis* differ primarily from plants of the female parent selection in flower color as flowers of plants of the female parent selection are white in color.

Plants of the new *Phalaenopsis* can be compared to plants of the male parent selection. Plants of the new *Phalaenopsis* differ primarily from plants of the male parent selection in flower color as plants of the male parent selection are violet in color with distinct venation. In addition, plants of the new *Phalaenopsis* are more freely flowering.

Plants of the new *Phalaenopsis* can be compared to plants of *Phalaenopsis hybrida* 'Phalalodu', not patented. In side-by-side comparisons conducted in Lochristi, Belgium, plants of the new *Phalaenopsis* differ primarily from plants of 'Phalalodu' in flower color as flowers of the new *Phalaenopsis* have a less distinct venation pattern. Additionally, plants of the new *Phalaenopsis* are more freely flowering than plants of 'Phalalodu'.

BRIEF DESCRIPTION OF THE PHOTOGRAPHS

The accompanying photographs illustrate the overall appearance of the new *Phalaenopsis* plant showing the colors as true as it is reasonably possible to obtain in colored reproductions of this type. Colors in the photographs may differ slightly from the color values cited in the detailed botanical description which accurately describe the colors of the new *Phalaenopsis* plant.

The photograph on the first sheet is a side perspective view of a typical flowering plant of 'MI00599' grown in a container.

The photograph at the top of second sheet is a close-up view of a typical inflorescence of 'MI00599'.

The photograph at the bottom of second sheet is a close-up view of a typical flower of 'MI00599'.

DETAILED BOTANICAL DESCRIPTION

The aforementioned photographs and following observations and measurements describe plants grown during the spring in 12-cm containers in a glass-covered greenhouse in Lochristi, Belgium and under cultural practices typically used in commercial *Phalaenopsis* production. During the production of the plants, day and night temperatures ranged from 18° C. to 29° C. and light levels ranged from 150 Watt/$m^2$ to 375 Watt/$m^2$. Plants were 76 weeks from propagation when the photographs and description were taken. In the following description, color references are made to The Royal Horticultural Society Colour Chart, 2015 Edition, except where general terms of ordinary dictionary significance are used.

Botanical classification: *Phalaenopsis hybrida* 'MI00599'.

Parentage:

- *Female parent*.—Proprietary selection of *Phalaenopsis hybrida* identified as code number PH00743, not patented.
- *Male parent*.—Proprietary selection of *Phalaenopsis hybrida* identified as code number PHM00230, not patented.

Propagation:

- *Type*.—By in vitro propagation (tissue culture).
- *Time to initiate roots, summer*.—About nine to ten weeks at temperatures about 26° C.
- *Time to initiate roots, winter*.—About ten to eleven weeks at temperatures about 26° C.
- *Time to produce a rooted young plant, summer*.—About 140 to 160 days at temperatures about 26° C.
- *Time to produce a rooted young plant, winter*.—About 150 to 180 days at temperatures about 26° C.
- *Root description*.—Thick, fleshy; typically grey green in color, towards the apex, close to light green; actual color of the roots dependent on substrate composition, water quality, fertilizer, substrate temperature and age of roots.
- *Rooting habit*.—Non-branching; sparse.

Plant description:

- *Plant form and growth habit*.—Herbaceous epiphyte; upright plant habit with typically two to three branched racemes per plant, each inflorescence with numerous flowers; monopodial; moderately vigorous growth habit and moderate growth rate; easy to produce.
- *Plant height, substrate level to top of foliar plane*.—About 18.8 cm.
- *Plant height, substrate level to top of inflorescences*.—About 45.5 cm.
- *Plant diameter or spread*.—About 34.8 cm.

Leaf description:

- *Arrangement and quantity*.—Distichous, simple; sessile; about seven per plant.
- *Length*.—About 17.9 cm.
- *Width*.—About 6.7 cm.
- *Aspect*.—Arching.
- *Shape*.—Narrowly obovate to elliptic; slightly carinate.
- *Apex*.—Broadly acute, unequal.
- *Base*.—Sheathing.
- *Margin*.—Entire; slightly revolute.
- *Texture and luster, upper surface*.—Smooth, glabrous; slightly glossy.
- *Texture and luster, lower surface*.—Slightly furrowed, glabrous; matte.
- *Venation pattern*.—Camptodromous.
- *Color*.—Developing leaves, upper surface: Close to 147A. Developing leaves, lower surface: Close to 147B. Fully expanded leaves, upper surface: Close to NN137B; venation, close to between 137A and darker than 146A. Fully expanded leaves, lower surface: Close to between 146B and 147B; venation, close to 146A.

Inflorescence description:

- *Appearance and flowering habit*.—Showy zygomorphic flowers arranged on axillary branched racemes; typically two to three racemes per plant; each inflorescence with about 15 flowers; flowers face outwardly to slightly nodding on arching inflorescences supported by strong upright peduncles; flowers with three petals, one petal transformed into a labellum and three sepals.
- *Fragrance*.—None detected.
- *Time to flower*.—Plants begin flowering about 18 weeks after an inductive cooling period.
- *Flower longevity*.—Individual flowers maintain good substance for about three months on the plant; flowers not persistent.
- *Inflorescence length* (*lowermost flower to inflorescence apex*).—About 20.6 cm.
- *Inflorescence width*.—About 24.1 cm.
- *Flower buds*.—Height: About 1.6 cm. Diameter: About 1.4 cm. Shape: Broadly ovate. Color: Close to 151A and 151B; venation, close to 187B.
- *Flower diameter*.—About 7.9 cm by 7.3 cm.
- *Flower depth*.—About 2.6 cm.
- *Petals, quantity and arrangement*.—Three, two lateral petals and one lower petal transformed into a labellum.
- *Lateral petals*.—Length: About 3.9 cm. Width: About 4.8 cm. Shape: Reniform. Apex: Rounded. Margin: Entire. Texture and luster, upper and lower surfaces: Glabrous, velvety; matte. Color: When opening, upper surface: Close to NN155D; towards the base, close to between 72B and 77B; venation, close to between 72B and 77B. When opening, lower surface: Close to NN155D; venation, close to 72B. Fully opened, upper surface: Close to NN155D; towards the base, close to 72B; venation, close to 72B; color does not fade with development. Fully opened, lower surface: Close to NN155D; venation, close to 72B; color does not fade with development.
- *Labellum*.—Appearance: Tri-lobed with two lateral lobes and a central lobe. Length, lateral and central lobes: About 2.1 cm. Width, lateral lobes: About 1.5 cm. Width, central lobe: About 2.3 cm. Shape, lateral lobes: Obovate. Shape, central lobe: Short deltoid to triangular. Apex, lateral lobes: Obtuse. Apex, central lobe: Cleft with two long narrow recurved cirrose tips. Margins, lateral lobes: Entire, slightly undulate. Margins, central lobe: Entire. Texture and luster, upper and lower surfaces: Glabrous, velvety; matte. Callosities: Located at the base of the labellum and attachment point of the lateral petals; about 4 mm in length, about 7 mm in width and about 6 mm in height. Color: When opening, upper surface: Lateral lobes: Close to NN155D; towards the basal margins, tinged with close to 8B to 8C; venation, close to between N78B and NN78B. Central lobe: Close to NN155D; towards the margins, cirrose apices and venation, close to N78A; adjacent to cirrose apices, close to 13B. Callosities: Close to 12B; fine dots, close to 183B. When opening, lower surface: Lateral lobes: Close to NN155D; towards the basal margins, tinged with close to 10A; venation, close to 77B. Central lobe: Close to NN155D; towards the cirrose apices, close to N80A; adjacent to cirrose apices, close to 10A; venation, close to N78A to N78B. Fully opened, upper surface: Lateral lobes: Close to NN155D; towards the basal margins, tinged with close to 10A; venation, close to between N78A. Central lobe: Close to NN155D; towards the margins, cirrose apices and venation, close to N78A; adjacent to cirrose apices, close to 13B. Callosities: Close to 12B; fine dots, close to 183B. Fully opened, lower surface: Lateral lobes: Close to NN155D; towards the basal margins, tinged with close to 10A; venation, close to 77B. Central lobe: Close to NN155D; towards the cirrose apices, close to N80A; adjacent to cirrose apices, close to 10A; venation, close to N78A to N78B.

*Sepals, quantity and arrangement*.—Three, two lower lateral sepals and one upper dorsal sepal. Length, lateral and dorsal sepals: About 4 cm. Width, lateral sepals: About 2.7 cm. Width, dorsal sepal: About 3 cm. Shape, lateral and dorsal sepals: Ovate. Apex, lateral sepals: Bluntly acute. Apex, dorsal sepal: Obtuse. Base, lateral and dorsal sepals: Obtuse to truncate. Margin, lateral and dorsal sepals: Entire. Texture and luster, lateral and dorsal sepals, upper and lower surfaces: Glabrous, velvety; matte. Color, lateral sepals: When opening, upper surface: Close to NN155D; towards the base, fine dots, close to 77A; venation, close to between 72B and 77B. When opening, lower surface: Close to NN155D; venation, close to 72B. Fully opened, upper surface: Close to NN155D; towards the base, fine dots, close to 77A; venation, close to 72B; color does not fade with development. Fully opened, lower surface: Close to NN155D; venation, close to 72B; color does not fade with development. Color, dorsal sepal: When opening, upper surface: Close to NN155D; towards the base, close to between 72B and 77B; venation, close to between 72B and 77B. When opening, lower surface: Close to NN155D; venation, close to 72B. Fully opened, upper surface: Close to NN155D; towards the base, close to 72B; venation, close to 72B; color does not fade with development. Fully opened, lower surface: Close to NN155D; venation, close to 72B; color does not fade with development.

*Peduncles*.—Length: About 49.9 cm. Diameter: About 4.5 mm. Strength: Very strong. Aspect: Upright to about 30° from vertical. Texture and luster: Smooth, glabrous; matte. Color: Close to between 147A and N199A heavily dotted with close to 147D.

*Pedicels*.—Length: About 3.5 cm. Diameter: About 3 mm. Strength: Moderately strong. Aspect: About 60° from peduncle axis. Texture and luster: Smooth, glabrous; matte. Color: Close to 150A to 150B; distally, close to 150D; proximally, close to 152A to 152B.

*Reproductive organs*.—Androecium: Column length: About 9 mm. Column width: About 6 mm. Column color: Close to NN155D; towards the apex, blushed and tinged with close to 77B. Pollinia quantity: Two. Pollinia diameter (per two pollinia): About 2 mm. Pollinia color: Close to 23A. Gynoecium: Stigma length: About 2.5 mm. Stigma width: About 4 mm. Stigma shape: Reniform. Stigma color: Close to NN155C. Ovary length: About 7.8 mm. Ovary diameter: About 2 mm. Ovary color: Close to lighter than 145D. Seeds and fruits: Seed and fruit development have not been observed on plants of the new *Phalaenopsis* to date.

Disease & pest resistance: Plants of the new *Phalaenopsis* have not been shown to be resistant to pathogens and pests common to *Phalaenopsis* plants to date.

Temperature tolerance: Plants of the new *Phalaenopsis* have been observed to tolerate high temperatures of about 40° C. and suitable for USDA Hardiness Zone 10.

It is claimed:

1. A new and distinct *Phalaenopsis* plant named 'MI00599' as illustrated and described.

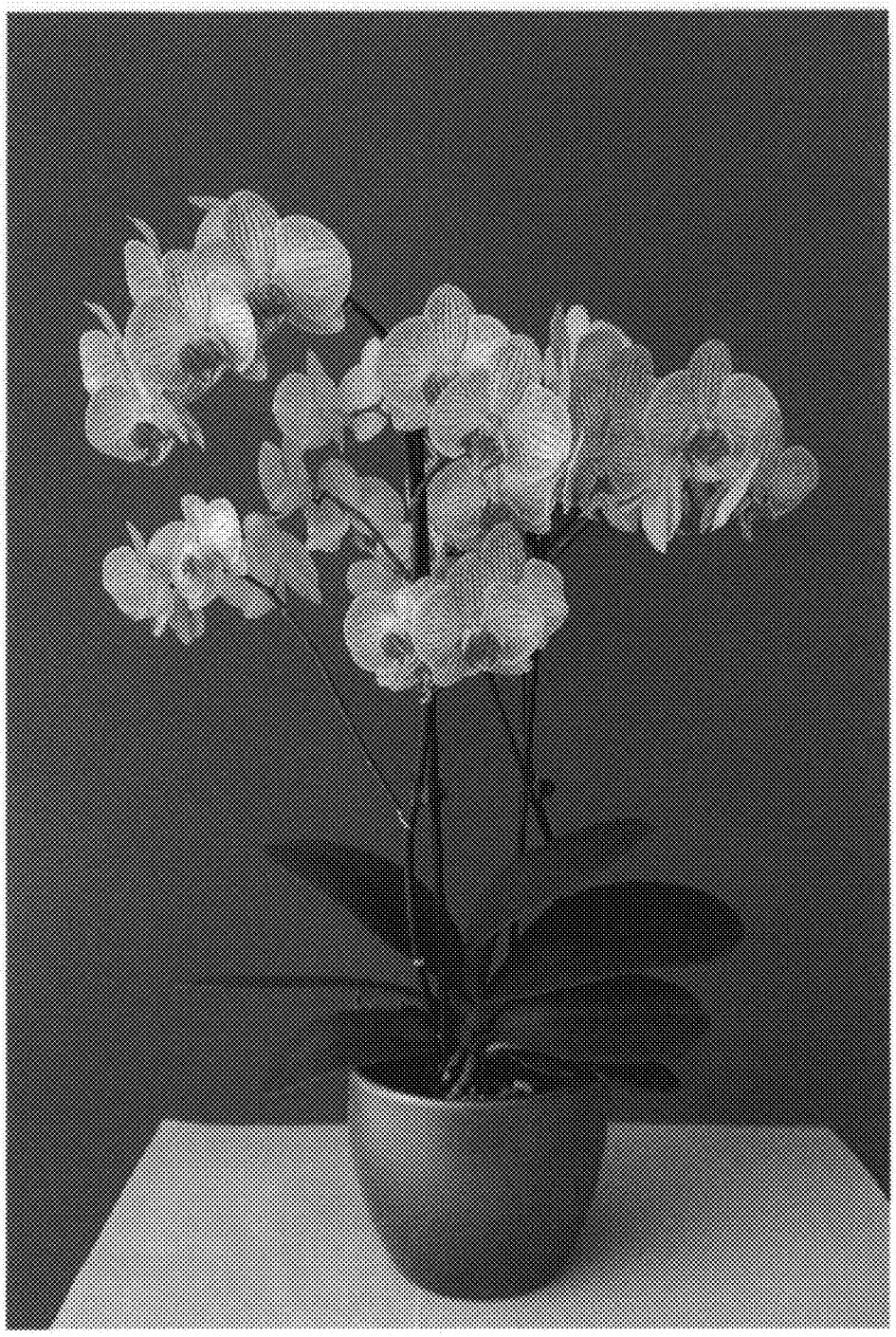

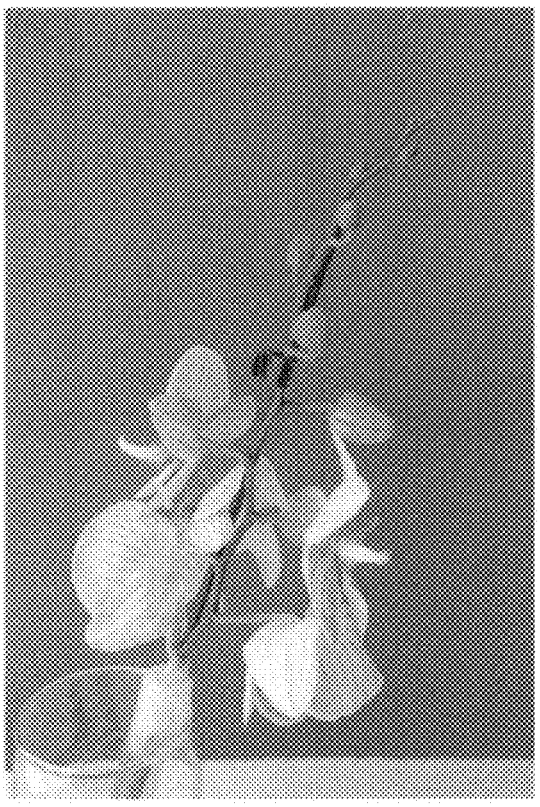
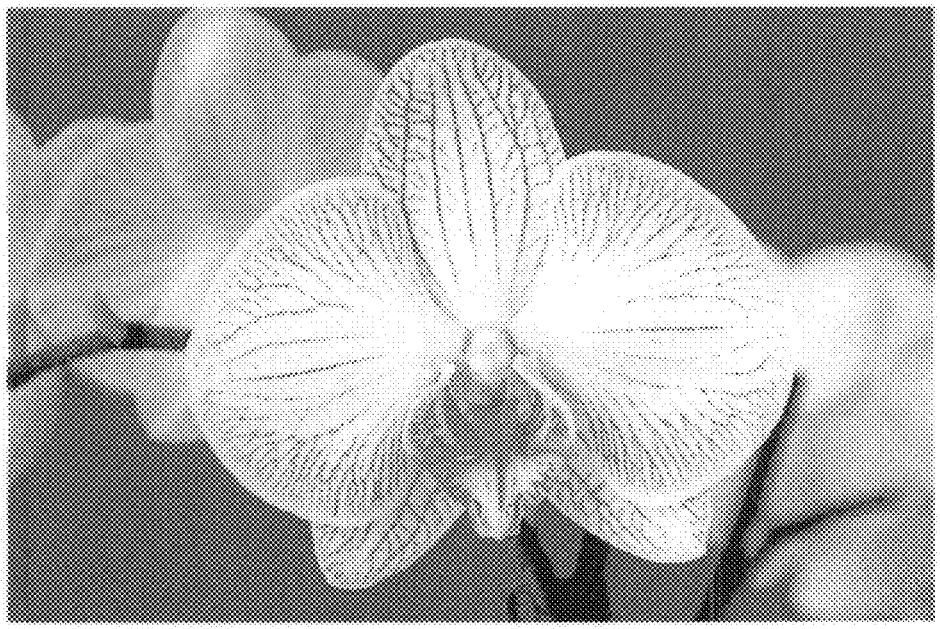

* * * * *